United States Patent [19]

Edwards

[11] 3,991,081
[45] *Nov. 9, 1976

[54] FUNGICIDAL 2-(N-HALOALKYLTHIOSULFONAMIDO)-THIOPHENES

[75] Inventor: Laroy H. Edwards, Napa, Calif.

[73] Assignee: Chevron Research Company, San Francisco, Calif.

[ * ] Notice: The portion of the term of this patent subsequent to June 10, 1992, has been disclaimed.

[22] Filed: May 19, 1975

[21] Appl. No.: 578,852

[52] U.S. Cl. .............................. 260/329 S; 424/275; 260/332.5
[51] Int. Cl.² .......................................... C07D 333/00
[58] Field of Search ................. 260/329 S; 424/275

[56] References Cited
UNITED STATES PATENTS 3,888,879   6/1975   Edwards ........................ 260/329 S Primary Examiner—James O. Thomas, Jr.
Assistant Examiner—A. Siegel
Attorney, Agent, or Firm—G. F. Magdeburger; Dix A. Newell; Raymond Owyang

[57] ABSTRACT

Novel thiophenes of the formula

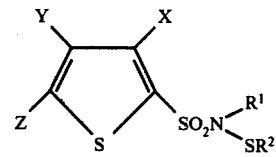

wherein X, Y and Z individually are hydrogen, lower alkyl, nitro, fluoro, chloro or bromo; $R^1$ is hydrogen, alkyl or aryl and $R^2$ is haloalkyl, are useful for the prevention or cure of fungal infections.

18 Claims, No Drawings

FUNGICIDAL 2-(N-HALOALKYLTHIOSULFONAMIDO)THIOPHENES

DESCRIPTION OF THE PRIOR ART

French Pat. No. 1,563,736, issued Apr. 18, 1969, to Pillon et al., discloses pesticidal 2-sulfonamido-3,4,5-trichlorothiophenes. A. Buzas et al., "Ann. Pharm. France" 19, 449 (1961) [C.A. 56, 6603c (1962)] discloses diuretic 2-sulfonamidothiophenes.

DESCRIPTION OF THE INVENTION

The thiophenes of the invention are represented by the formula

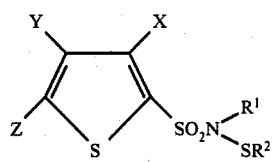

wherein X is hydrogen, alkyl of 1 to 3 carbon atoms, nitro, fluoro, chloro or bromo; Y is hydrogen, alkyl of 1 to 3 carbon atoms, nitro, fluoro, chloro or bromo; Z is H, alkyl of 1 to 3 carbon atoms, fluoro, chloro or bromo; $R^1$ is hydrogen, alkyl of 1 to 6 carbon atoms, phenyl substituted with up to 2 (0 to 2) of the same or different substituents selected from trifluoromethyl, trichloromethyl, fluoro, chloro, bromo, nitro or alkyl of 1 to 3 carbon atoms; and $R^2$ is haloalkyl of 1 to 3 carbon atoms and 1 to 7 of the same or different halogens of atomic number 9 to 35 (fluoro, chloro or bromo).

Representative alkyl $R^1$ groups are methyl, ethyl, propyl, isopropyl, butyl and hexyl. Representative substituted phenyl $R^1$ groups are o-trifluoromethylphenyl, m-trifluoromethylphenyl, p-trichloromethylphenyl, o-fluorophenyl, m-chlorophenyl, p-bromophenyl, 2,4-dichlorophenyl, 3,5-dibromophenyl, 3-bromo-4-chlorophenyl, o-tolyl, 2,4-dimethylphenyl, p-nitrophenyl and 2-chloro-4-methylphenyl. Representative haloalkyl $R^2$ groups are chloromethyl, trifluoromethyl, dichloromethyl, trichloromethyl, fluorodichloromethyl, tribromoethyl, 2,2,2-trichloroethyl, 1,2,2,2-tetrachloroethyl, 1,1,2,2-tetrabromoethyl, pentachloroethyl, 2,2,3,3,3-pentabromopropyl and 3,3,3-trichloropropyl.

The preferred X and Z groups are hydrogen, methyl, chloro or bromo. The preferred Y group is hydrogen or nitro. The preferred $R^1$ group is lower alkyl of 1 to 3 carbon atoms, phenyl or phenyl substituted with 1 or 2 trifluoromethyl or trichloromethyl. The preferred $R^2$ group is polyhaloalkyl of 1 to 2 carbon atoms and 2 to 5 of the same or different halogens selected from chloro or bromo.

A preferred class of thiophenes of formula (I) is that wherein X is hydrogen; Y is nitro; Z is chloro or bromo; $R^1$ is alkyl of 1 to 3 carbon atoms or phenyl substituted with up to 2 trifluoromethyl, fluoro or chloro, and $R^2$ is polyhaloalkyl of 1 to 2 carbon atoms and 2 to 5 of the same or different halogens selected from chloro or bromo.

Another preferred class of thiophenes of formula (I) is that wherein X is lower alkyl of 1 to 3 carbon atoms; Y and Z are hydrogen; $R^1$ is alkyl of 1 to 3 carbon atoms or phenyl substituted with up to 2 trifluoromethyl, fluoro or chloro and $R^2$ is polyhaloalkyl of 1 to 2 carbon atoms and 2 to 5 of the same or different halogens selected from chloro or bromo.

The thiophenes of the invention are prepared by reacting a thienylsulfonyl chloride (II) with an amine or aniline compound (III), and sulfenylating the resulting sulfonamidothiophene (IV) with a haloalkylsulfenyl halide (V) in the presence of an acid acceptor. These reactions are depicted in reactions (1) and (2):

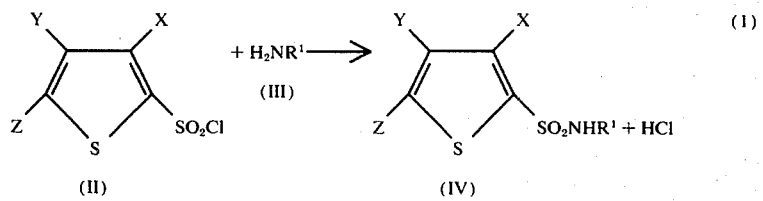

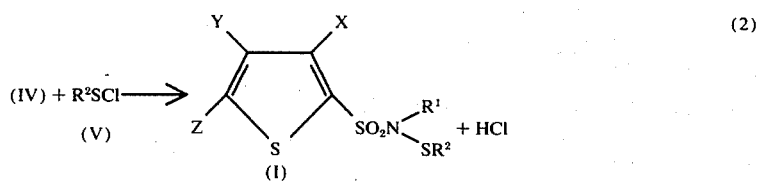

wherein X, Y, Z, $R^1$ and $R^2$ have the same significance as previously defined, $SR^3$ is a haloalkylthio $R^2$ group as previously defined, and B is an acid acceptor.

Reaction (1) is conducted by reacting substantially equimolar quantities of the thienylsulfonyl chloride (II) and the amine or aniline (III) in an inert diluent at a temperature of 0° to 100° C. If desired, a molar excess of the amine or aniline (III), or an acid acceptor as defined below, can be used as an acid acceptor for the hydrogen chloride produced in the reaction. Reaction (2) is conducted by reacting substantially equimolar quantities of the sulfonamidothiophene (IV) and the sulfenyl halide (V) in the presence of an acid acceptor. Suitable acid acceptors are organic amines such as pyridine compounds, e.g., pyridine or alpha-picoline, and lower trialkylamines, e.g., triethylamine or tripropylamine. Generally, at least one mcl of acid acceptor is employed for each mol of sulfenyl halide. The reaction is normally conducted in an inert liquid diluent, e.g., organic solvents such as chlorinated hydrocarbons. The product (I) is isolated and purified by conventional procedures such as extraction, filtration, crystallization and chromatography.

The halo- and alkyl-substituted thienylsulfonyl chlorides of formula (II) are prepared by sulfonating a thiophene with chlorosulfonic acid. The nitro-substituted thienylsulfonyl chlorides of formula II are suitably prepared by nitrating a thienylsulfonyl chloride with nitric acid in a suitable solvent such as concentrated sulfuric acid or acetic anhydride.

The compounds of the invention are useful for controlling fungi, particularly plant fungal infections caused by *Botrytis cinerea*, leaf blights caused by organisms such as *Septoria apii*, *Alternaria solani conidia* and *Phytophthora infestans conidia*, powdery mildew caused by organisms such as *Erysiphe polygoni* and *E. chicoraciarum*, and other fungal infections caused by organisms such as *Pythrium ultimum*, *Helminthosporum sativum*, *Fusarium moniliforme*, *Rhizoctonia solani*, *Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divide particles which disperse readily in water or other dispersant. These compositions normally contain from about 5–80% fungicide, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1 to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of these techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

EXAMPLE 1

Preparation of 3-methyl-2-(N-methyl-N-1,1,2,2-tetrachloroethylthio)thiophene

A 49-g (0.5 mol) sample of 3-methylthiophene was added in small portions to a cooled solution (−20° C) of 128 g (1 mol) chlorosulfonic acid in 250 cc chloroform. After the addition was completed, the reaction mixture was allowed to warm to about 25° C and then heated at reflux for 30 minutes. The reaction mixture was then diluted with ice water and neutralized with aqueous sodium bicarbonate solution. The organic layer was separated, dried over magnesium sulfate and evaporated to give 30 g of 3-methyl-2-thienylsulfonyl chloride.

An aqueous solution of 23.8 g (0.306 mol) methylamine was added dropwise to 30 g (0.153 mol) 3-methyl-2-thienylsulfonyl chloride. The resulting reaction mixture was stirred and heated at 50° C for 2 hours. The reaction mixture was then diluted with methylene chloride, washed with water, dried over magnesium sulfate and evaporated to give the crude 3-methyl-2-N-methylsulfonamidothiophene product. After crystallization from petroleum-ether, the product melted at 73°–74° C.

A 7.65-g (0.0328 mol) sample of 1,1,2,2-tetrachlorosulfenyl chloride was added to a cooled solution (0° C) of 6.2 g (0.0328 mol) 3-methyl-2-N-methylsulfonamidothiophene in 200 cc methylene chloride. To the resulting solution was then added dropwise 3.6 g (0.036 mol) triethylamine. The reaction mixture was then stirred at about 25° C for 1 ½ hours and at a reflux for 2 hours. The reaction mixture was washed with water, dried over magnesium sulfate and evaporated to give an oil. Crystallization of the oil from petroleum-ether gave 6 g of 3-methyl-2-(N-methyl-N-1,1,2,2-tetrachloroethylthiosulfonamido)thiophene, m.p. 65°–67° C.

EXAMPLE 2

Preparation of 5-methyl-4-nitro-2-(N-3,5-di-trifluoromethylphenylsulfonamido)thiophene A 25.2 g (0.1 mcl) sample of 5-methyl-2-thienylsulfonyl chloride was added slowly to a solution of 100 cc concentrated sulfuric acid and 100 cc concentrated nitric acid. The resulting mixture was allowed to stir overnight at about 25° C. The reaction mixture was then added to ice water and filtered to give the 5-methyl-4-nitro-2-thienylsulfenyl chloride product.

A mixture of 12 g (0.05 mol) 5-methyl-4-nitro-2-thienylsulfonyl chloride and 22 g (0.1 mol) 3,5-di-trifluoromethylaniline was stirred at ambient temperature (about 25° C) overnight. The reaction mixture was then eluted through a silica-gel column with 50% ether-hexane to give the 5-methyl-4-nitro-2-(N-3,5-di-trifluoromethylphenylsulfonamido)thiophene product, m.p. 165°–167° C.

Other compounds of the invention were prepared by the procedures of Examples 1–2. These compounds and the compounds of Example 1–2 are tabulated in Table I.

EXAMPLE 3

Tomato Late Blight

Representative compounds of the invention were tested for the control of the Tomato Late Blight organism *Phytophthora infestans conidia*. Five- to six-week-old tomato (variety Bonny Best) seedlings were used. The tomato plants were sprayed with a 250-ppm solution of the test compound in acetone, water, and a small amount of a non-ionic emulsifier. The sprayed plants were then inoculated one day later with the organism, placed in an environmental chamber and incubated at 66°–68° F and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The test compounds and the results are tabulated in Table II.

EXAMPLE 4

Tomato Early Blight

Representative compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a non-ionic emulsifier. The sprayed plants were inoculated one day later with the organism, dried and maintained at 60–80% relative humidity for about 12 days. Percent disease control was based on the percent disease development on untreated check plants. The compounds tested and the results are tabulated in Table III.

EXAMPLE 5

Powdery Mildew Control

Representative compounds of the invention were tested for powdery mildew control using pinto-bean plants. The pathogen was *Erysiphe polygoni*. The pinto-bean plants were sprayed with a 250-ppm solution of the test compound in an acetone-water mixture containing a nonionic emulsifier. One day after spraying, the treated plants were inoculated with the pathogen and then maintained in a greenhouse at a 60–80% relative humidity. The rate of infection on the leaves was determined after about 10 days. The percent disease control provided by a given test compound was based on the disease reduction relative to untreated check plants. The results are reported in Table IV.

TABLE I

Compounds of the Formula 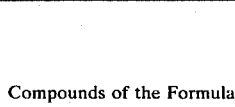

| No. | X | Y | Z | R¹ | R³ | Melting Point, °C | Sulfur Calc. | Sulfur Found | Chlorine Calc. | Chlorine Found |
|---|---|---|---|---|---|---|---|---|---|---|
| 1 | H | NO$_2$ | Cl | H | H | 153–155 | 26.4 | 26.3 | 14.7 | 15.2 |
| 2 | H | NO$_2$ | Cl | i-C$_3$H$_7$ | H | 109–110 | 22.5 | 21.8 | 12.5 | 12.7 |
| 3 | H | NO$_2$ | Cl | φ | H | 123–127 | 20.1 | 19.6 | 11.1 | 11.0 |
| 4 | H | NO$_2$ | Cl | CH$_3$ | H | 108–111 | 13.8 | 12.5 | 24.5 | 24.2 |
| 5 | CH$_3$ | H | H | CH$_3$ | H | 73–74 | 33.5 | 32.8 | — | — |
| 6 | H | H | CH$_3$ | CH$_3$ | H | 35–36 | 33.5 | 32.8 | — | — |
| 7 | CH$_3$ | H | H | φ | H | 95–97 | 25.3 | 24.1 | — | — |
| 8 | H | H | CH$_3$ | φ | H | 49–50 | 25.3 | 23.9 | — | — |
| 9 | CH$_3$ | H | H | p-CF$_3$—φ | H | 87–89 | 20.0 | 20.0 | — | — |
| 10 | H | H | CH$_3$ | p-CF$_3$—φ | H | 106–108 | 20.0 | 20.2 | — | — |
| 11 | H | NO$_2$ | Cl | p-CF$_3$—φ | H | 137–140 | 16.6 | 17.2 | — | — |
| 12 | H | NO$_2$ | CH$_3$ | p-CF$_3$—φ | H | 112–114 | 17.5 | 16.2 | — | — |
| 13 | CH$_3$ | H | NO$_2$ | p-CF$_3$—φ | H | 104–106 | 17.5 | 17.1 | — | — |
| 14 | Br | H | H | p-CF$_3$—φ | H | 98–100 | 16.6 | 16.5 | — | — |
| 15 | H | NO$_2$ | CH 3 | 3,5-(CF$_3$)$_2$—φ | H | 165–167 | 14.8 | 15.3 | — | — |
| 16 | Br | H | H | 3,5-(CF$_3$)$_2$—φ | H | 100–102 | 14.1 | 15.3 | — | — |

TABLE I-continued

Compounds of the Formula

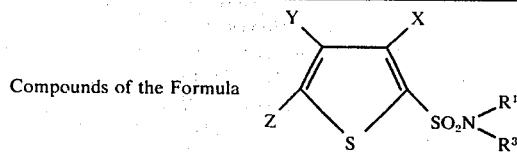

| No. | X | Y | Z | R¹ | R³ | Melting Point, °C | Sulfur Calc. | Sulfur Found | Chlorine Calc. | Chlorine Found |
|---|---|---|---|---|---|---|---|---|---|---|
| 17 | Br | $NO_2$ | H | p-$CF_3$—φ | H | 153–155 | 14.9 | 15.1 | — | — |
| 18 | H | H | Br | p-$CF_3$—φ | H | 103–104 | 16.6 | 16.7 | — | — |
| 19 | $CH_3$ | $NO_2$ | H | p-$CF_3$—φ | H | 136–138 | 17.5 | 18.0 | — | — |
| 20 | H | H | Cl | p-$CF_3$—φ | H | 92–94 | 18.8 | 19.1 | 10.4 | 10.4 |
| 21 | $CH_3$ | $NO_2$ | H | 3,5-$(CF_3)_2$—φ | H | 133–134 | 10.8 | 10.9 | — | — |
| 22 | $CH_3$ | H | $NO_2$ | 3,5-$(CF_3)_2$—φ | H | 152–153 | 13.2 | 13.2 | — | — |
| 23 | H | H | Cl | $CH_3$ | —$SCCl_3$ | 70–71 | 26.6 | 26.8 | 39.3 | 38.3 |
| 24 | H | H | Cl | $CH_3$ | —$SCCl_2CCl_2H$ | 51–52 | 23.5 | 23.6 | 43.3 | 41.3 |
| 25 | H | H | Cl | φ | —$SCCl_3$ | 122–124 | 22.7 | 23.3 | 33.5 | 31.1 |
| 26 | H | H | Cl | φ | —$SCCl_2CCl_2H$ | 152–154 | 20.4 | 20.1 | 37.6 | 37.1 |
| 27 | H | $NO_2$ | Cl | $CH_3$ | —$SCCl_2CCl_2H$ | 93–94 | 21.2 | 21.0 | 39.0 | 37.6 |
| 28 | H | $NO_2$ | Cl | $CH_3$ | —$SCCl_3$ | 109–111 | 23.7 | 23.6 | 34.9 | 34.8 |
| 29 | H | $NO_2$ | Cl | i-$C_3H_7$ | —$SCCl_3$ | 81–83 | 22.2 | 22.0 | 32.7 | 33.0 |
| 30 | H | $NO_2$ | Cl | i-$C_3H_7$ | —$SCCl_2CCl_2H$ | 108–109 | 19.9 | 21.4 | 36.7 | 38.9 |
| 31 | H | $NO_2$ | Cl | φ | —$SCCl_2CCl_2H$ | 148–150 | 18.6 | 18.0 | 34.3 | 33.6 |
| 32 | H | $NO_2$ | Cl | φ | —$SCCl_3$ | 135–137 | 20.6 | 19.1 | 30.3 | 30.6 |
| 33 | $CH_3$ | H | H | $CH_3$ | —$SCCl_2CCl_2H$ | 65–67 | 24.7 | 24.2 | 36.4 | 34.9 |
| 34 | $CH_3$ | $NO_2$ | H | p-$CF_3$—φ | —$SCCl_3$ | 105–107 | 18.7 | 19.2 | 20.6 | 20.6 |

TABLE II
Tomato Late Blight Control

| No. | % Control |
|---|---|
| 23 | 44 |
| 24 | 44 |
| 27 | 96 |
| 28 | 93 |
| 34 | 64 |

TABLE III
Tomato Early Blight Control

| No. | % Control |
|---|---|
| 25 | 51 |
| 27 | 100 |
| 28 | 85 |
| 29 | 80 |
| 32 | 93 |
| 33 | 98 |

TABLE IV
Powdery Mildew Control

| No. | % Control |
|---|---|
| 24 | 62 |
| 25 | 93 |
| 27 | 57 |
| 28 | 100 |
| 29 | 92 |

What is claimed is:

1. A compound of the formula

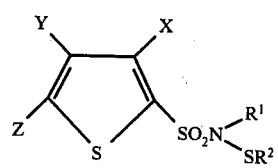

wherein X is hydrogen, fluoro, chloro, bromo, nitro or alkyl of 1 to 3 carbon atoms; Y is hydrogen, fluoro, chloro, bromo, nitro or alkyl of 1 to 3 carbon atoms; Z is hydrogen, fluoro, chloro, bromo, nitro or alkyl of 1 to 3 carbon atoms; R¹ is hydrogen, alkyl of 1 to 6 carbon atoms or phenyl substituted with up to 2 of the same or different groups selected from trifluoromethyl, trichloromethyl, fluoro, chloro, bromo, nitro or alkyl of 1 to 6 carbon atoms; and R² is haloalkyl of 1 to 3 carbon atoms and 1 to 7 of the same or different halogens selected from fluoro, chloro or bromo.

2. The compound of claim 1 wherein R² is polyhaloalkyl of 1 to 2 carbon atoms and 2 to 5 of the same or different halogens selected from chloro or bromo.

3. The compound of claim 2 wherein R² is trichloromethyl and tetrachloroethyl.

4. The compound of claim 2 wherein X and Z are hydrogen, methyl, chloro or bromo.

5. The compound of claim 2 wherein Y is hydrogen or nitro.

6. The compound of claim 2 wherein R¹ is alkyl of 1 to 3 carbon atoms.

7. The compound of claim 2 wherein R¹ is phenyl or phenyl substituted with 1 to 2 trifluoromethyl or trichloromethyl.

8. The compound of claim 7 wherein X is alkyl of 1 to 3 carbon atoms, Y an Z are hydrogen and R¹ is alkyl of 1 to 3 carbon atoms.

9. 3-methyl-2-(N-methyl-N-1,1,2,2-tetrachloroethylthiosulfonamido)thiophene, according to claim 1.

10. A method for controlling fungi which comprises contacting said fungi or their habitats with a fungicidally effective amount of the compound defined in claim 1.

11. The method of claim 10 wherein R² is polyhaloalkyl of 1 to 2 carbon atoms and 2 to 5 of the same or different halogens selected from chloro or bromo.

12. The method of claim 10 wherein R² is trichloromethyl or tetrachloroethyl.

13. The method of claim 10 wherein X and Z are hydrogen, methyl, chloro or bromo.

14. The method of claim 10 wherein Y is hydrogen or nitro.

15. The method of claim 10 wherein $R^1$ is alkyl of 1 to 3 carbon atoms.

16. The method of claim 10 wherein $R^1$ is phenyl or phenyl substituted with 1 to 2 trifluoromethyl or trichloromethyl.

17. The method of claim 11 wherein X is alkyl of 1 to 3 carbon atoms, Y and Z are hydrogen and $R^1$ is alkyl of 1 to 3 carbon atoms.

18. The method of claim 10 wherein the compound is 3-methyl-2-(N-methyl-N-1,1,2,2-tetrachloroethylthiosulfonamido)thiophene.

* * * * *